United States Patent [19]

Hoffmann et al.

[11] 3,975,523

[45] Aug. 17, 1976

[54] O-(2-CARBISOPROPOXYPHENYL)-THIONO-PHOSPHORIC (PHOSPHONIC) ACID ESTER-AMIDES AND ESTER-IMIDES AND INSECTICIDAL AND ACARICIDAL COMPOSITION AND METHOD

[75] Inventors: Hellmut Hoffmann, Wuppertal; Ingeborg Hammann, Cologne; Bernhard Homeyer, Opladen, all of Germany

[73] Assignee: Bayer Aktiengesellschaft, Leverkusen, Germany

[22] Filed: July 30, 1974

[21] Appl. No.: 493,201

[30] Foreign Application Priority Data

Aug. 8, 1973 Germany............................ 2340080

[52] U.S. Cl............................ 424/212; 260/240 G; 260/941
[51] Int. Cl.² ...................... A01N 9/36; C07F 9/24; C07F 9/44
[58] Field of Search.................... 260/941; 424/212

[56] References Cited
UNITED STATES PATENTS

| | | | |
|---|---|---|---|
| 3,621,082 | 11/1971 | Schrader et al..................... | 260/941 |
| 3,806,559 | 4/1974 | Hofer et al.......................... | 26/941 |
| 3,882,103 | 5/1975 | Beriger et al. ................. | 260/941 X |

*Primary Examiner*—Richard L. Raymond
*Attorney, Agent, or Firm*—Burgess, Dinklage & Sprung

[57] ABSTRACT

O-(2-Carbisopropoxyphenyl)-thiono-phosphoric(-phosphonic) acid ester-amides and ester-imides of the formula

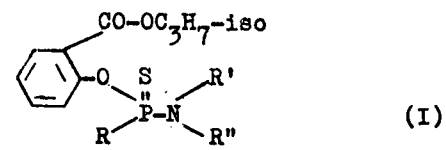

in which
  R is lower alkyl or alkoxy,
  R' is hydrogen, and
  R'' is a formyl or acetyl radical, or
  R' and R'' conjointly form an aminomethylene, monoalkylaminomethylene or dialkylaminomethylene radical with 1 to 6 carbon atoms in each alkyl chain, or a phenylaminomethylene or heterocyclic aminomethylene radical, or a lower alkoxymethylene radical,
which possess insecticidal and acaricidal properties.

9 Claims, No Drawings

O-(2-CARBISOPROPOXYPHENYL)-THIONO-PHOSPHORIC (PHOSPHONIC) ACID ESTER-AMIDES AND ESTER-IMIDES AND INSECTICIDAL AND ACARICIDAL COMPOSITION AND METHOD

The present invention relates to and has for its objects the provision of particular new O-(2-carbisopropoxyphenyl)-thiono-phosphoric(phosphonic) acid ester-amides and ester-imides, i.e. O-(2-carbisopropoxy-phenyl)-thionophosphoric acid ester N-formyl or N-acetyl amides, N-aminomethylene-imides, N-alkoxymethylene-imides, and their alkanephosphonic acid ester amide and imide counterparts, which possess insecticidal or acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from Belgian Patent Specification No. 724,681 that O-phenyl-O-alkyl-thiono-phosphoric acid esteramides, for example O-methyl- (Compound A) or O-ethyl-N-methyl- (Compound B) or O-ethyl-N,N-dimethyl-O-(2-carbisopropoxy-phenyl)- (Compound C), O-methyl-O-(2-carbisopropoxyphenyl)- (Compound D) or O-ethyl-O-(2-carbocycloheoxyphenyl (Compound E) or 2-carboethoxy-phenyl (Compound F) or 2-carbopropoxyphenyl (Compound G) or 2-carbo-sec.-butoxyphenyl)-thiono-phosphoric acid ester-amide (Compound H), possess insecticidal and acaricidal properties.

The present invention provides, as new compounds, the O-phenyl-thionophosphoric(phosphonic) acid ester-amide and ester-imide derivative of the formula

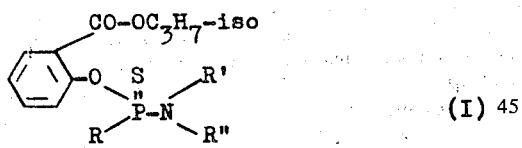

in which
R is lower alkyl or alkoxy,
R' is hydrogen, and
R'' is a formyl or acetyl radical, or
R' and R'' conjointly form an aminomethylene, monoalkylaminomethylene or dialkylamino-methylene radical with 1 to 6 carbon atoms in each alkyl chain, or a phenylaminomethylene or heterocyclic aminomethylene radical, or a lower alkoxymethylene radical.

Preferably the lower alkyl and alkoxy radicals of R or R'+R'' are alkoxy, each with 1 to 4, especially 1 to 3, carbon atoms.

Surprisingly, the O-phenyl-thionophosphoric(phosphonic) acid ester-amide and ester-imide derivatives of the formula (I) possess a substantially better insecticidal, including soil-insecticidal, and acaricidal action than prior art compounds of analogous structure and of the same type of action. The compounds according to the invention thus represent a genuine enrichment of the art.

The present invention also provides a process for the preparation of an O-phenylthionophosphoric(phosphonic) acid ester-amide or ester-imide derivative of the formula (I), in which
(a) an O-phenyl-thionophosphoric(phosphonic) acid ester-amide of the general formula

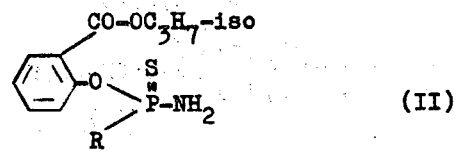

is reacted with acetic anhydride or with a dialkoxy compound of the general formula

or (b) a phosphorylated iminoformic acid alkyl ester of the general formula

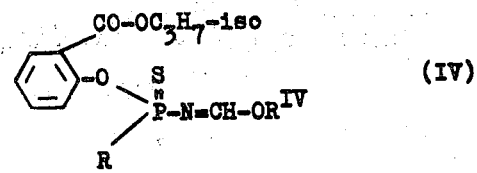

is reacted with ammonia or a primary or secondary amine of the general formula

or a compound of the formula (IV) is hydrolyzed partially; in which formulas (II) to (V)
R has the above-mentioned meaning,
Alk is alkyl,
R''' is dialkylamino or alkoxy,
$R^{IV}$ is alkyl with 1 to 4 carbon atoms,
$R^V$ is hydrogen or alkyl and
$R^{VI}$ is hydrogen or an alkyl, phenyl or heterocyclic radical.

If, for example, O-ethyl-O-[2-carbisopropoxyphenyl]-thionophosphoric acid ester-amide and acetic anhydride, ortho-formic acid triethyl ester or N,N-diethylformamide-dimethylacetal, or N-[O-(2-carbisopropoxyphenyl)-O-ethylthiophosphoryl]-iminoformic acid ethyl ester and diethylamine or water, are used as starting compounds, the course of the reactions in the various process variants can be represented by the following equations:

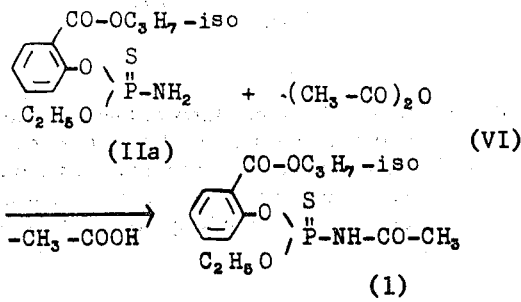

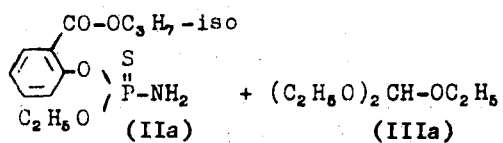

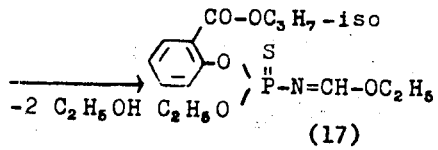

(VII)

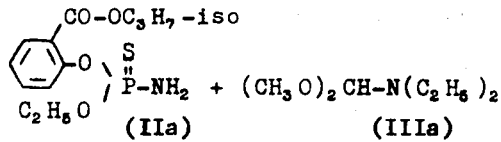

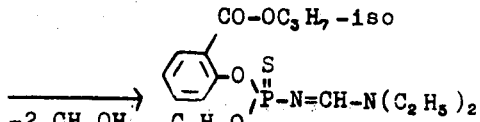

(VIII)

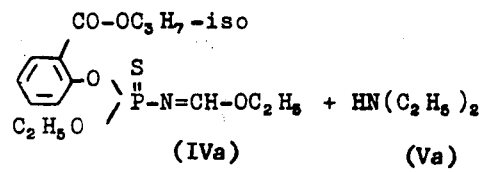

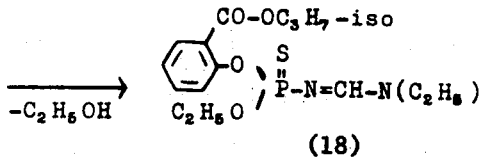

(IX)

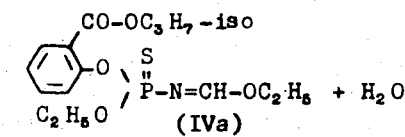

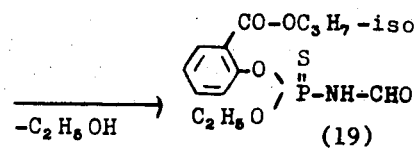

(XI)

R''' in formula (III) is preferably di-lower alkylamino with 1 to 4 carbon atoms in each alkyl radical or alkoxy with 1 to 3 carbon atoms; $R^V$ in formula (V) is preferably hydrogen or alkyl with 1 to 4 carbon atoms; and $R^{VI}$ in formula (V) is preferably hydrogen, alkyl with 1 to 4 carbon atoms, phenyl, pyrrole or pyridine.

O-Phenyl-thionophosphoric(phosphonic) acid ester-amides (II) to be used as starting compounds are already described in the literature and are obtainable according to customary processes as described, for example, in Belgian Pat. No. 724,681; similarly, the ortho-formic acid alkyl ester derivatives (III) can be prepared as described, for example, in Chemische Berichte, Vol. 101 (1968) page 46.

The following may be mentioned as examples of the compounds (II) and (III): O-methyl-, O-ethyl-, O-n-propyl- or O-isopropyl-O-(2-carbisopropoxyphenyl)-thionophosphoric acid ester-amide; methane-, ethane-, n-propane- or isopropane-O-(2-carbisopropoxyphenyl)-thionophosphonic acid ester-amide; ortho-formic acid methyl, ethyl, n-propyl, isopropyl and mixed ester; and N,N-(dimethyl-, diethyl-, di-n-propyl, di-isopropyl-, di-n-butyl-, di-sec.-butyl-, di-tert.-butyl or methyl-butyl)-formamide-dimethyl-, -diethyl- or methyl-ethyl-acetal.

The alkylamines, phenylamines and heterocyclic amines (V) required as starting compounds according to process variant (b) are also known from the literature and can also be prepared easily on an industrial scale.

The following may be mentioned as examples of these: methylamine, ethylamine, n-propylamine, isopropylamine, n-, sec.-, tert.- or iso-butylamine, dimethylamine, diethylamine, di-n-propylamine, di-isopropylamine, di-n-butylamine, di-sec.-butylamine, di-tert.-butylamine, di-iso-butylamine, aniline, pyrrolylamine, pyridylamine, and ammonia.

Examples of phosphorylated iminoformic acid alkyl esters (IV) to be employed in accordance with process variant (b) are: N-[O-(2-carbisopropoxyphenyl)-O-methyl-, -O-ethyl-, -O-n-propyl-, -O-isopropyl-, -O-n-butyl-, -O-sec.-butyl-, -O-iso-butyl- or -O-tert.-butyl-thiophosphoryl]-iminoformic acid methyl ester, the corresponding ethyl and propyl esters, and N-[O-(2-carbisopropoxyphenyl)-thio-methane-, -ethane-, -n-propane-, -isopropane-, -n-butane-, -isobutane- or -sec.-butane-phosphonyl]-iminoformic acid methyl ester, as well as the corresponding ethyl esters and propyl esters.

The process of preparation can optionally be carried out with conjoint use of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

In process variant (a), when acetic anhydride or an ortho-formic acid alkyl ester is one of the reactants, the reaction can be carried out in the presence of an acid catalyst such as, for example, toluenesulfonic acid or sulphuric acid.

The reaction temperature can be varied within a fairly wide range. In general, process variant (a) is carried out at between 60° and 200°C, preferably at about 100° to 180°C; process variant (b) is generally effected at between 0° and 150°C, preferably at about 10° to 50°C. The reactions are generally allowed to take place under normal pressure.

To carry out process variant (a), the two components are preferably combined in the absense of a solvent or diluent, but if acetic anhydride or an ortho-formic acid ester is used, the process is carried out in the presence of an acid catalyst, with the dialkoxy component (III) in most cases being added in 10 to 25% excess. The reaction mixture is then heated to the stated temperatures for one or more hours, the alcohol formed, if any, is distilled off at the same time, and finally the mixture is worked up according to customary methods.

In process variant (b), the reactants are in general employed in the equivalent ratio; they are mixed, in most cases, in the presence of a solvent, and the mixture is further stirred for one or more hours at the stated temperatures and is then worked up in the usual manner.

The new compounds are in some cases obtained in the form of oils which can mostly not be distilled without decomposition but can be freed of the last volatile constituents by so-called "slight distillation," that is to say prolonged heating under reduced pressure to moderately elevated temperatures, and can be purified in this way. They are characterized by the refractive index. some of the products are obtained in a crystalline form, in which case they are characterized by their melting points.

As has already been mentioned, the O-phenyl-thionophosphoric(phosphonic) acid ester-amide and ester-imide derivatives according to the invention are distinguished by an outstanding insecticidal, including soil-insecticidal, and acaricidal activity. They couple a low phytotoxicity with a good action against both sucking and biting insects and against mites (Acarina); in addition, some of them display fungicidal properties.

For this reason, the compounds according to the invention can be employed with success in plant protection and as pesticides in the hygiene field and the field of protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphic (*Macrosiphum solanifolii*), the current gall aphid (*Cryptomyzus korschelti*), the rosy apple aphid (*Sappaphis mali*), the mealy plum aphid (*Hyalopterus arundinis*) and the cherry blackfly (*Myzus cerasi*); in addition, scales and mealy bugs (Coccina), for example the oleander scale (*Aspidiotus hederae*) and the soft scale (*Lecanium hesperidum*) as well as the grape mealy bug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly catapillars (*Lepidoptera*) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutwork (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Maderia cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as Henschoutedenia flexivitta; further, the Orthoptera, for example the house cricket (*Gryllus domesticus*); termites such as the eastern subterranean termite (*Reticulitermes flavipes*) and *Hymenoptera* such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (*Tetranychidae*) such as the two-spotted spider mite (*Tetranychus urticae*) and the European red mite (*Paratetranychus pilosus* = *Panonychus ulmi*), gall mites, for example the black-current gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the present compounds are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally wit the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ester, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or rodenticides, fungicides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these geneally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e., an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The outstanding activity and unexpected superiority of the particular new compounds of the present invention are illustrated, without limitation, by the following examples:

EXAMPLE 1

Phaedon larvae test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specific periods of time, the degree of destruction is determined in %: 100% means that all of the beetle larvae were killed whereas 0% means that none of the beetle larvae were killed.

The active compounds, the concentrations of the active compounds, the evaluation times and the results can be seen from the following Table 1:

Table 1

| Active compound | (*Phaedon* larvae test) Active compound concentration in % | Degree of destruction in % after 3 days |
|---|---|---|
| 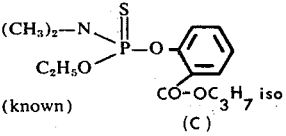 (known) (C) | 0.1<br>0.01<br>0.001 | 100<br>40<br>0 |
| 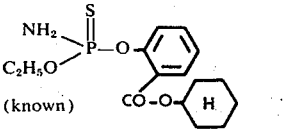 (known) (E) | 0.1<br>0.01 | 100<br>0 |
| 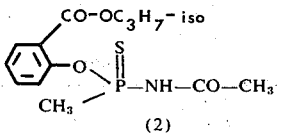 (2) | 0.1<br>0.01<br>0.001 | 100<br>100<br>65 |
| 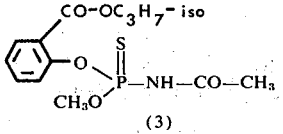 (3) | 0.1<br>0.01<br>0.001<br>0.0001 | 100<br>100<br>100<br>100 |
| 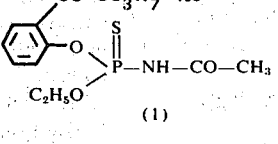 (1) | 0.1<br>0.01<br>0.001 | 100<br>100<br>100 |

Table 1-continued (*Phaedon* larvae test)

| Active compound | Active compound concentration in % | Degree of destruction in % after 3 days |
|---|---|---|
| (7) 2-(iso-C$_3$H$_7$O-CO)-C$_6$H$_4$-O-P(=S)(OCH$_3$)-N=CH-OCH$_3$ | 0.1<br>0.01<br>0.001 | 100<br>100<br>100 |
| (5) 2-(iso-C$_3$H$_7$O-CO)-C$_6$H$_4$-O-P(=S)(OCH$_3$)-N=CH-OC$_2$H$_5$ | 0.1<br>0.01<br>0.001 | 100<br>100<br>100 |
| (6) 2-(iso-C$_3$H$_7$O-CO)-C$_6$H$_4$-O-P(=S)(CH$_3$)-N=CH-OC$_2$H$_5$ | 0.1<br>0.01<br>0.001 | 100<br>100<br>100 |
| (8) 2-(iso-C$_3$H$_7$O-CO)-C$_6$H$_4$-O-P(=S)(OCH$_3$)-N=CH-NH-C(CH$_3$)$_3$ | 0.1<br>0.01<br>0.001 | 100<br>100<br>30 |
| (13) 2-(iso-C$_3$H$_7$O-CO)-C$_6$H$_4$-O-P(=S)(OCH$_3$)-N=CH-N(C$_2$H$_5$)$_2$ | 0.1<br>0.01<br>0.001 | 100<br>100<br>30 |
| (12) 2-(iso-C$_3$H$_7$O-CO)-C$_6$H$_4$-O-P(=S)(OCH$_3$)-N=CH-NH-(2-pyridyl) | 0.1<br>0.01<br>0.001 | 100<br>100<br>85 |
| (4) 2-(iso-C$_3$H$_7$O-CO)-C$_6$H$_4$-O-P(=S)(OCH$_3$)-NH-CHO | 0.1<br>0.01<br>0.001 | 100<br>100<br>55 |

EXAMPLE 2

Plutella test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed, whereas 0% means that none of the caterpillars were killed.

The active compounds, the concentrations of the active compounds, the evaluation times and the results can be seen from the following Table 2:

Table 2

(*Plutella* test)

| Active compound | Active compound concentration in % | Degree of destruction in % after 3 days |
|---|---|---|
| (E) (known) — NH₂, C₂H₅O–P(=S)–O–C₆H₄–CO–O–C₆H₁₁ | 0.1<br>0.01 | 100<br>0 |
| (F) (known) — NH₂, C₂H₅O–P(=S)–O–C₆H₄–CO–OC₂H₅ | 0.1<br>0.01<br>0.001 | 100<br>80<br>0 |
| (H) (known) — NH₂, C₂H₅O–P(=S)–O–C₆H₄–CO–OCH(CH₃)(C₂H₅) | 0.1<br>0.01<br>0.001 | 100<br>100<br>0 |
| (G) (known) — NH₂, C₂H₅O–P(=S)–O–C₆H₄–CO–OC₃H₇ | 0.1<br>0.01<br>0.001 | 100<br>100<br>0 |
| (A) (known) — CH₃–NH, CH₃O–P(=S)–O–C₆H₄–CO–OC₃H₇ iso | 0.1<br>0.01<br>0.001 | 100<br>100<br>0 |
| (B) (known) — CH₃–NH, C₂H₅O–P(=S)–O–C₆H₄–CO–OC₃H₇ iso | 0.1<br>0.01<br>0.001 | 100<br>100<br>0 |
| (C) (known) — (CH₃)₂–N, C₂H₅O–P(=S)–O–C₆H₄–CO–OC₃H₇ iso | 0.1<br>0.01<br>0.001 | 100<br>100<br>0 |
| (3) — iso-C₃H₇O–CO–C₆H₄–O–P(=S)(OCH₃)–NH–CO–CH₃ | 0.1<br>0.01<br>0.001 | 100<br>100<br>85 |

Table 2-continued

| (Plutella test) | | |
|---|---|---|
| Active compound | Active compound concentration in % | Degree of destruction in % after 3 days |
| ![compound 5: benzene ring with CO-OC₃H₇-iso, O, CH₃O, P(=S)-N=CH-OC₂H₅] (5) | 0.1<br>0.01<br>0.001 | 100<br>100<br>95 |
| ![compound 6: benzene ring with CO-OC₃H₇-iso, O, CH₃, P(=S)-N=CH-OC₂H₅] (6) | 0.1<br>0.01<br>0.001 | 100<br>100<br>95 |

EXAMPLE 3

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed, whereas 0% means that none of the aphids were killed.

The active compounds, the concentrations of the active compounds, the evaluation times and the results can be seen from the following Table 3:

Table 3

| (Myzus test) | | |
|---|---|---|
| Active compound | Active compound concentration in % | Degree of destruction in % after 1 day |
| ![compound E: NH₂, C₂H₅O, P(=S)-O-benzene-CO-O-cyclohexyl] (known) (E) | 0.1 | 0 |
| ![compound A: CH₃-NH, CH₃O, P(=S)-O-benzene-CO-OC₃H₇iso] (known) (A) | 0.1<br>0.01 | 50<br>0 |
| ![compound C: (CH₃)₂-N, C₂H₅O, P(=S)-O-benzene-CO-OC₃H₇iso] (known) (C) | 0.1<br>0.01 | 60<br>0 |
| ![compound 2: benzene with CO-OC₃H₇-iso, O, CH₃, P(=S)-NH-CO-CH₃] (2) | 0.1<br>0.01 | 100<br>65 |

Table 3-continued
(*Myzus* test)

| Active compound | Active compound concentration in % | Degree of destruction in % after 1 day |
|---|---|---|
| Compound (3): 2-(iso-$C_3H_7$O-CO)-phenyl O-methyl N-acetyl phosphoramidothioate, $CH_3O$-P(=S)(O-aryl)-NH-CO-$CH_3$ | 0.1<br>0.01 | 100<br>60 |
| Compound (7): aryl O-methyl, P(=S)-N=CH-O$CH_3$ | 0.1<br>0.01 | 100<br>97 |
| Compound (5): aryl O-methyl, P(=S)-N=CH-O$C_2H_5$ | 0.1<br>0.01<br>0.0001 | 100<br>100<br>30 |
| Compound (6): aryl, $CH_3$, P(=S)-N=CH-O$C_2H_5$ | 0.1<br>0.01<br>0.001 | 100<br>100<br>90 |
| Compound (14): aryl O-methyl, P(=S)-N=CH-NH-$CH_3$ | 0.1<br>0.01 | 100<br>100 |
| Compound (8): aryl O-methyl, P(=S)-N=CH-NH-C($CH_3$)$_3$ | 0.1<br>0.01 | 99<br>80 |
| Compound (13): aryl O-methyl, P(=S)-N=CH-N($C_2H_5$)$_2$ | 0.1<br>0.01 | 98<br>40 |
| Compound (16): aryl O-methyl, P(=S)-N=CH-NH-phenyl | 0.1<br>0.01 | 99<br>30 |
| Compound (10): aryl, $CH_3$, P(=S)-N=CH-N($CH_3$)$_2$ | 0.1<br>0.01 | 100<br>30 |

(All compounds have the aryl group 2-(iso-$C_3H_7$O-CO)-phenyl-O-)

Table 3-continued (Myzus test)

| Active compound | Active compound concentration in % | Degree of destruction in % after 1 day |
|---|---|---|
| 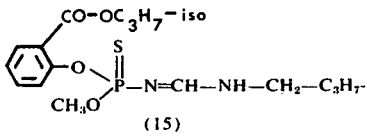 (15) | 0.1<br>0.01 | 99<br>50 |

EXAMPLE 4

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed, whereas 0% means that none of the spider mites were killed.

The active compounds, the concentrations of the active compounds, the evaluation times and the results can be seen from the following Table 4:

Table 4

(*Tetranychus* test / resistant)

| Active compound | Active compound concentration in % | Degree of destruction in % after 2 days |
|---|---|---|
| 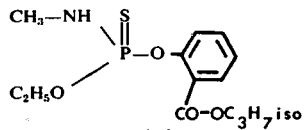 (B) (known) | 0.1 | 0 |
| 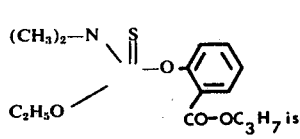 (C) (known) | 0.1 | 0 |
| 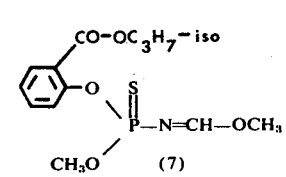 (7) | 0.1 | 98 |
| 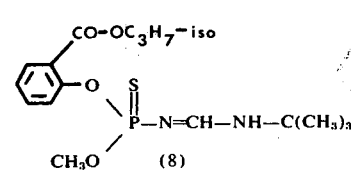 (8) | 0.1<br>0.01 | 98<br>50 |
| 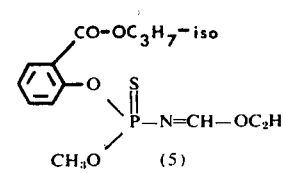 (5) | 0.1<br>0.01 | 90<br>70 |

Table 4-continued (*Tetranychus* test / resistant)

| Active compound | Active compound concentration in % | Degree of destruction in % after 2 days |
|---|---|---|
| 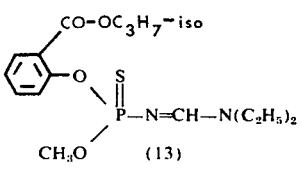 (13) | 0.1 | 100 |
| 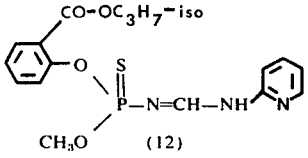 (12) | 0.1 | 90 |
| 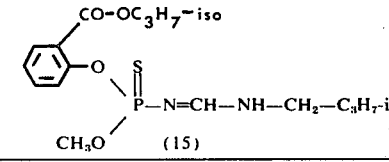 (15) | 0.1 | 98 |

EXAMPLE 5

Critical concentration test/soil insects

Test insect: Tenebrio molitor larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration. The preparation of active compound was intimately mixed with the soil. The concentration of the active compound in the preparation was practically immaterial, the only decisive factor being the amount by weight of active compound per unit volume of soil, which is quoted in ppm (for example mg/l). The soil was filled into pots and the pots were left to stand at room temperature. After 24 hours the test insects were introduced into the treated soil and after a further 48 hours the degree of effectiveness of the active compound was determined in % by counting the dead and live test insects. The degree of effectiveness was 100% if all test insects had been killed and was 0% if exactly as many test insects were still alive as in the case of the control.

The active compounds, amounts used and results can be seen from the Table 5 which follows:

Table 5

(Test with *Tenebrio molitor* larvae in the soil)

| Active compound | Degree of destruction in % at an active-compound concentration of | | | | |
|---|---|---|---|---|---|
| | 20 | 10 | 5 | 2.5 | 1.25 ppm |
| 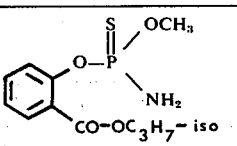 (known) (D) | 0 | | | | |
| 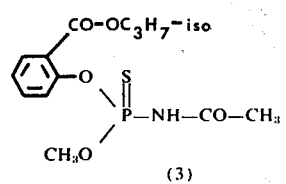 (3) | 100 | 100 | 95 | 50 | |
| 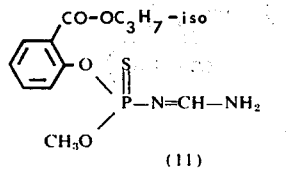 (11) | 100 | 100 | 100 | 90 | 50 |

Table 5-continued (Test with *Tenebrio molitor* larvae in the soil)

| Active compound | Degree of destruction in % at an active-compound concentration of | | | | |
|---|---|---|---|---|---|
| | 20 | 10 | 5 | 2.5 | 1.25 ppm |
| Compound (7): 2-(isopropoxycarbonyl)phenyl O-methyl N-(methoxymethylene)phosphoramidothioate | 100 | 100 | 95 | 50 | |
| Compound (2): 2-(isopropoxycarbonyl)phenyl methyl N-acetylphosphoramidothioate | 100 | 100 | 95 | 50 | |
| Compound (1): 2-(isopropoxycarbonyl)phenyl O-ethyl N-acetylphosphoramidothioate | 100 | 100 | 100 | 100 | 90 |

EXAMPLE 6

Critical concentration test/soil insects

Test insect: Phorbia brassicae grubs
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration. The preparation of active compound was intimately mixed with the soil. The concentration of the active compound in the preparation was practically immaterial, the only decisive factor being the amount by weight of active compound per unit volume of soil, which is quoted in ppm (for example mg/1). The soil was filled into pots and the pots were left to stand at room temperature. After 24 hours the test insects were introduced into the treated soil and after a further 48 hours the degree of effectiveness of the active compound was determined in % by counting the dead and live test insects. The degree of effectiveness was 100% if all test insects had been killed and was 0% if exactly as many test insects were still alive as in the case of the control.

The active compounds, amounts used and the results can be seen from the Table 6 which follows:

Table 6

(Test with *Phorbia brassicae* grubs in the soil)

| Active compound | Degree of destruction in % at an active compound concentration of | | | |
|---|---|---|---|---|
| | 20 | 10 | 5 | 2.5 ppm |
| (known) 2-(n-propoxycarbonyl)phenyl O-ethyl phosphoramidothioate | | | 0 | |
| (known) O-ethyl phosphoramidothioate derivative | | | 0 | |

Table 6-continued (Test with *Phorbia brassicae* grubs in the soil)

| Active compound | Degree of destruction in % at an active compound concentration of | | | |
|---|---|---|---|---|
| | 20 | 10 | 5 | 2.5 ppm |
| 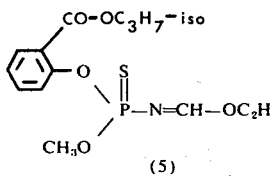 (5) | 100 | 100 | 95 | 50 |
| 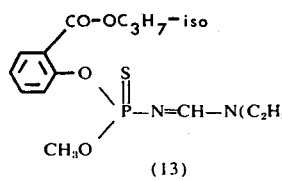 (13) | 100 | 100 | 95 | 50 |
| 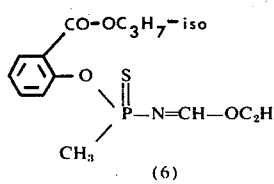 (6) | 100 | 100 | 95 | 50 |
| 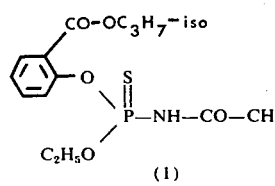 (1) | 100 | 100 | 100 | 50 |

The process of this invention is illustrated in the following preparative Examples.

EXAMPLE 7 a.

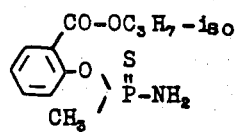 (IIb)

Ammonia was introduced into a solution of 60 g (0.2 mole) of O-(2-carbisopropoxyphenyl)-thionomethanephosphonic acid ester chloride in 300 ml of acetonitrile at 15°–20°C until the mixture reacted weakly alkaline. After stirring for 1 hour, the mixture was poured into water and the product was taken up in benzene. The organic phase was washed and then dried and the solvent was distilled off and the residue subjected to "slight distillation". 38 g (70% of theory) of O-(2-carbisopropoxyphenyl)-thionomethanephosphonic acid ester-amide of refractive index $n_D^{21}$ of 1.5503 were obtained.

The following compounds could be prepared analogously:

| | Physical data (melting point, °C) | Yield (% of theory) |
|---|---|---|
| 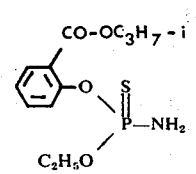 (IIa) | 58 | 92 |
| 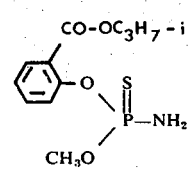 (IIc) | 44 | 67 |

EXAMPLE 1:

b.

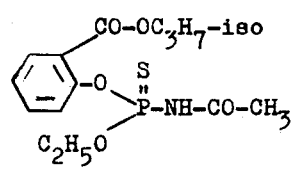 (1)

Two drops of concentrated sulfuric acid were added to a mixture of 30 g (0.1 mole) of O-ethyl-O-(2-carbisopropoxyphenyl)-thionophosphoric acid ester-amide and 12 g of acetic anhydride, whereupon the internal temperature rose to 48°C. The reaction mixture was cooled and taken up in benzene and the benzene solution was then washed with water and sodium bicarbonate solution until it reacted neutral. After drying the organic phase, the solvent was evaporated off under reduced pressure and the residue was recrystallized from an ethyl acetate/ligroin mixture, whereupon 17 g (50% of theory) of O-ethyl-O-(2-carbisopropoxyphenyl-N-acetylthionophosphoric acid ester-amide of melting point 66°C were obtained.

The following compounds could be prepared analogously:

water was stirred overnight. The reaction mixture was then poured into benzene, the benzene solution was dried, the solvent was distilled off under reduced pressure and the residue was subjected to "slight distillation". This gave 26 g (82% of theory) of O-methyl-O-(2-carbisopropoxyphenyl)-N-formyl-thionophosphoric acid ester-amide of refractive index $n_D^{23}$ of 1.5381.

EXAMPLE 9

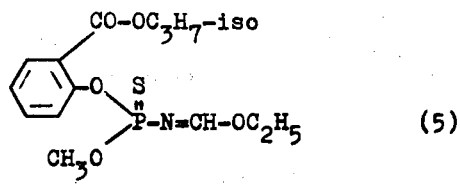

(5)

| Compound No. | | Melting point (°C) | Yield (% of theory) |
|---|---|---|---|
| 2 | ![structure with CO-OC₃H₇-iso, O, P-NH-CO-CH₃, CH₃] | 87 | 54 |
| 3 | ![structure with CO-OC₃H₇-iso, O, P-NH-CO-CH₃, CH₃O] | 74-76 | 74 |

EXAMPLE 8

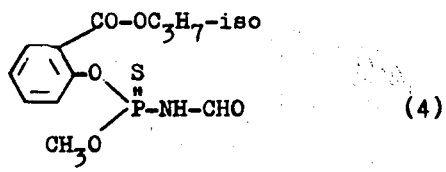

(4)

A mixture of 35 g (0.1 mole) of N-[O-methyl-O-(2-carbisopropoxyphenyl)-thionophosphoryl]-iminoformic acid ethyl ester, 100 ml of acetonitrile and 10 ml of A mixture of 289 g (1 mole) of O-methyl-O-(2-carbisopropoxyphenyl)-thionophosphoric acid ester-amide and 160 g of ortho-formic acid triethyl ester was heated, in the presence of 2 g of p-toluenesulfonic acid, for 3 hours to 120°C, and finally to 140°C, using a descending condenser (10 cm Vigreux column). The residue was subjected to "slight distillation" under reduced pressure. 319 g (92% of theory) of N-[O-methyl-O-(2-carbisopropoxyphenyl)-thiophosphoryl]-iminoformic acid ethyl ester of refractive index $n_D^{22}$ of 1.5286 were obtained.

The following compounds could be obtained by analogous methods:

| Compound No. | | Refractive index | Yield (% of theory) |
|---|---|---|---|
| 6 | ![structure with CO-OC₃H₇-iso, O, P-N=CH-OC₂H₅, CH₃] | $n_D^{23}$: 1.5394 | 79 |

-continued

| Compound No. | | Refractive index | Yield (% of theory) |
|---|---|---|---|
| 7 | 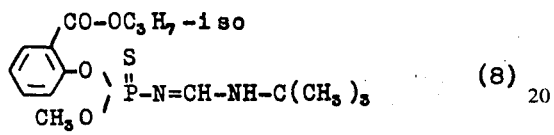 | $n_D^{24}$:1.5362 | 86 |

EXAMPLE 10

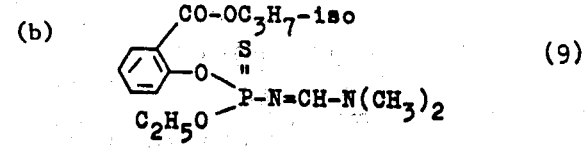  (8)

7.3 g of tert.-butylamine were added to 35 g (0.1 mole) of N-[O-methyl-O-(2-carbisopropoxyphenyl)-thiophosphoryl]-iminoformic acid ethyl ester in 100 ml of benzene at 10° – 15°C. After stirring the mixture for 2 hours, the solvent was evaporated off under reduced pressure and the residue was subjected to "slight distillation". 35 g (91% of theory) of O-methyl-O-(2-carbisopropoxyphenyl)-N-(N'-tert.-butylaminomethylene)-thionophosphoric acid ester-amide of refractive index $n_D^{24}$ of 1.5387 were obtained.

EXAMPLE 11 a. $(C_2H_5)_2N\text{-}CH(OCH_3)_2$ (IIIb)

985 g of dimethyl sulfate were added to 790 g (7.8 moles) of N,N-diethylformamide while stirring, in the course of which the internal temperature rose to 40°C. After the batch had been stirred overnight, the mixture was allowed to run into 7.8 moles of sodium methylate in methanol (total volume approximately 2.3 l) at 0° to 5°C, while stirring, and the reaction mixture was again stirred overnight. The methanol was then distilled from the crystal paste. The desired product was subsequently distilled off up to a bath temperature of 170°C under 10 mm Hg, and was then fractionally distilled through a column. 862 g (75% of theory) of N,N-diethylformamide-dimethylacetal of boiling point 70°C/50 mm Hg (foaming) and of refractive index $n_D^{24}$ of 1.4074 were obtained.

The following compounds could be prepared analogously:

| | yield (% of theory) | Boiling point |
|---|---|---|
| $(CH_3)_2N\text{—}CH(OCH_3)_2$ (IIIc) | 38 | 104°C/760 mm Hg |
| $(C_3H_7)_2N\text{—}CH(OCH_3)_2$ (IIId) | 59 | 44°C/2 mm Hg |

(b)

$$\underset{C_2H_5O}{\overset{\displaystyle\text{CO-OC}_3\text{H}_7\text{-iso}}{\underset{}{\text{-O}}}}\text{P-N=CH-N(CH}_3)_2 \quad (9)$$

A mixture of 30 g (0.1 mole) of O-ethyl-O-(2-carbisopropoxyphenyl)-thionophosphoric acid ester-amide and 20 g of N,N-dimethylformamide-dimethylacetal was heated for 2 hours under reflux. The alcohol produced was then distilled off under reduced pressure, whereupon 31 g (87% of theory) of O-ethyl-O-(2-carbisopropoxyphenyl)-N-(N',N'-dimethylaminomethylene)-thionophosphoric acid ester-amide of refractive index $n_D^{23}$ of 1.5457 were obtained.

The following compounds could be prepared by analogous methods:

Table 7

| Compound No. | | Physical data (refractive index, melting point) | Yield (% of theory) |
|---|---|---|---|
| 10 | ![structure with P—N=CH—N(CH₃)₂ and CH₃] | $n_D^{23}$:1.5603 | 82 |
| 11 | ![structure with P—N=CH—NH₂ and CH₃O] | 92–94°C | 76 |

Table 7-continued

| Compound No. | | Physical data (refractive index, melting point) | Yield (% of theory) |
|---|---|---|---|
| 12 | 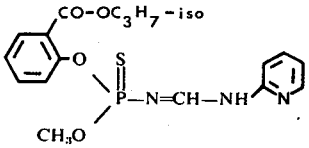 | $n_D^{24}: 1.5898$ | 81 |
| 13 | 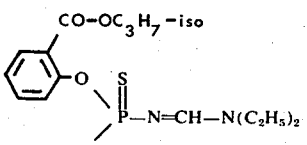 | $n_D^{24}: 1.5431$ | 97 |
| 14 | 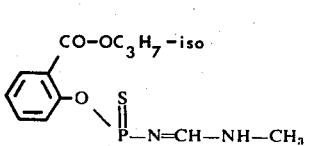 | $n_D^{23}: 1.5591$ | 88 |
| 15 | 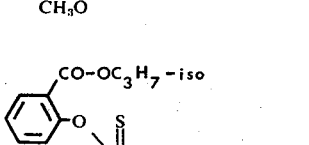 | $n_D^{24}: 1.5401$ | 86 |
| 16 | 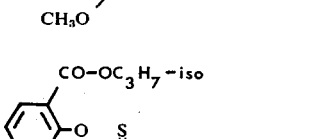 | $n_D^{24}: 1.5919$ | 72 |

It will be appreciated that the instant specification and examples are set forth by way of illustration and not limitation, and that various modifications and changes may be made without departing from the spirit and scope of the present invention.

What is claimed is:

1. An O-(2-carbisopropoxyphenyl)-thionophosphoric(phosphonic) acid ester amide or ester imide of the formula

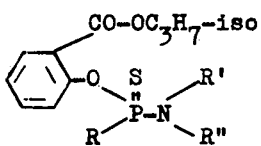

in which
R is lower alkyl or alkoxy,
R' is hydrogen, and
R'' is a formyl or acetyl radical, or
R' and R'' conjointly form lower alkoxymethylene radical.

2. A compound according to claim 1, in which R has 1 to 3 carbon atoms.

3. The compound according to claim 1 wherein such compound is O-(2-carbisopropoxyphenyl)-N-acetyl-methanethionophosphonic acid ester-amide of the formula

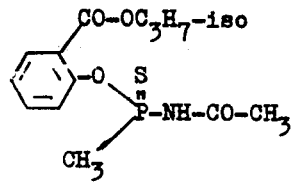

4. The compound according to claim 1 wherein such compound is O-methyl-O-(2-carbisopropoxyphenyl)-N-acetylthionophosphoric acid ester-amide of the formula

33

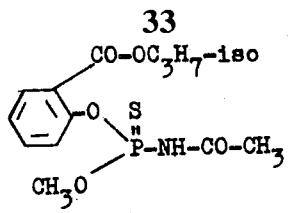

34

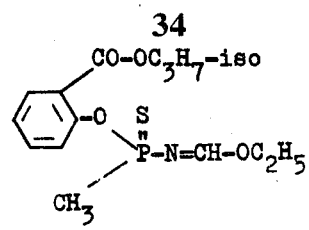

5. The compound according to claim 1 wherein such compound is N-[O-methyl-O-(2-carbisopropoxyphenyl)-thiophosphoryl]-iminoformic acid ethyl ester of the formula

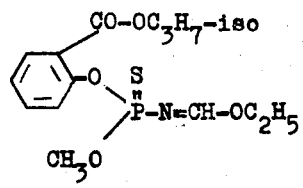

6. The compound according to claim 1 wherein such compound is N-[O-(2-carbisopropoxyphenyl)-thiomethanephosphonyl]-iminoformic acid ethyl ester of the formula 7. An insecticidal or acaricidal composition containing as active ingredient an insecticidally or acaricidally effective amount of a compound according to claim 1 in admixture with a diluent.

8. A method of combating insects or acarids which comprises applying to the insects or acarids or to a habitat thereof an insecticidally or acaricidally effective amount of a compound according to claim 1.

9. The method according to claim 8 in which said compound is

O-(2-carbisopropoxyphenyl)-N-acetylmethanethionophosphonic acid ester-amide,

O-methyl-O-(2-carbisopropoxyphenyl)-N-acetylthionophosphoric acid ester-amide,

N-[O-methyl-O-(2-carbisopropoxyphenyl)-thiophosphoryl]-iminoformic acid ethyl ester, or N-[O-(2-carbisopropoxyphenyl)-thio-methanephosphonyl]-iminoformic acid ethyl ester.

* * * * *